United States Patent
Forsell

(10) Patent No.: US 9,259,583 B2
(45) Date of Patent: Feb. 16, 2016

(54) COIL SYSTEM

(76) Inventor: Peter Forsell, Bouveret (CH)

( * ) Notice: Subject to any disclaimer, the term of this patent is extended or adjusted under 35 U.S.C. 154(b) by 915 days.

(21) Appl. No.: 13/384,039

(22) PCT Filed: Jul. 19, 2010

(86) PCT No.: PCT/SE2010/050857
§ 371 (c)(1), (2), (4) Date: Jan. 13, 2012

(87) PCT Pub. No.: WO2011/008163
PCT Pub. Date: Jan. 20, 2011

(65) Prior Publication Data
US 2012/0119700 A1 May 17, 2012

Related U.S. Application Data

(60) Provisional application No. 61/213,804, filed on Jul. 17, 2009.

(30) Foreign Application Priority Data

Jul. 17, 2009 (SE) ...................... 0901004

(51) Int. Cl.
*H02J 7/00* (2006.01)
*A61N 1/372* (2006.01)
(Continued)

(52) U.S. Cl.
CPC .......... *A61N 1/37229* (2013.01); *A61N 1/3787* (2013.01); *H01F 27/2823* (2013.01); *H01F 38/14* (2013.01); *H02J 5/005* (2013.01)

(58) Field of Classification Search
USPC ....................................................... 320/108
See application file for complete search history.

(56) References Cited

U.S. PATENT DOCUMENTS 6,456,883 B1 * 9/2002 Torgerson et al. ............... 607/34
6,463,329 B1 * 10/2002 Goedeke ......................... 607/60
(Continued)

FOREIGN PATENT DOCUMENTS

GB          291157       5/1928
WO     WO 03/039652    5/2003
(Continued)

OTHER PUBLICATIONS

International Search Report for PCT/SE2010/050857, mailed Oct. 21, 2010.
(Continued)

*Primary Examiner* — Edward Tso
*Assistant Examiner* — Robert Grant

(57) ABSTRACT

In supplying energy to a medical device implanted in a mammal patient a first coil system (20) external to the patient's body for wirelessly transferring energy can be used that inductively cooperates with a second coil system (12) that, when implanted in the patient's body, receives wirelessly transferred energy for supplying energy or control signals to the medical device, when implanted in the patient's body. The first and second coil systems comprise each at least two individual coils (50, 51; 60, 61) which are not directly electrically connected to each other and operate basically independently of each other. This may give a very efficient and versatile transfer of energy or control signals. The coils in each of the coil systems can be operating at different frequencies by being connected to respective electric circuits, where each of these respective electric circuits operate basically independently of each other generating e.g. alternating electric current of different frequencies.

20 Claims, 5 Drawing Sheets

(51) Int. Cl.
*A61N 1/378* (2006.01)
*H02J 5/00* (2006.01)
*H01F 27/28* (2006.01)
*H01F 38/14* (2006.01)

(56) References Cited

U.S. PATENT DOCUMENTS

| | | | |
|---|---|---|---|
| 2005/0288740 A1* | 12/2005 | Hassler et al. | 607/61 |
| 2006/0061323 A1 | 3/2006 | Cheng et al. | |
| 2010/0211133 A1 | 8/2010 | Forsell | |
| 2010/0211134 A1 | 8/2010 | Forsell | |
| 2010/0217352 A1 | 8/2010 | Forsell | |
| 2010/0217353 A1 | 8/2010 | Forsell | |
| 2010/0222848 A1 | 9/2010 | Forsell | |
| 2010/0222849 A1 | 9/2010 | Forsell | |
| 2010/0234922 A1 | 9/2010 | Forsell | |
| 2011/0193688 A1 | 8/2011 | Forsell | |
| 2011/0196452 A1 | 8/2011 | Forsell | |
| 2011/0278948 A1 | 11/2011 | Forsell | |
| 2011/0301668 A1 | 12/2011 | Forsell | |
| 2012/0112556 A1 | 5/2012 | Forsell | |

FOREIGN PATENT DOCUMENTS

WO WO 2007/143958 12/2007
WO WO 2009/051536 4/2009

OTHER PUBLICATIONS

U.S. Appl. No. 13/384,387 (Forsell), filed Jan. 17, 2012.
U.S. Appl. No. 13/130,648 (Forsell), filed Aug. 3, 2011.
U.S. Appl. No. 13/130,634 (Forsell), filed Aug. 3, 2011.
U.S. Appl. No. 13/123,638 (Forsell), filed Apr. 11, 2011.
U.S. Appl. No. 13/123,168 (Forsell), filed Apr. 7, 2011.
U.S. Appl. No. 12/738,182 (Forsell), filed Apr. 15, 2010.
U.S. Appl. No. 12/682,835 (Forsell), filed Apr. 13, 2010.
U.S. Appl. No. 12/682,831 (Forsell), filed Apr. 13, 2010.
U.S. Appl. No. 12/682,477 (Forsell), filed Apr. 9, 2010.
U.S. Appl. No. 12/682,404 (Forsell), filed Apr. 9, 2010.
U.S. Appl. No. 12/682,336 (Forsell), filed Apr. 9, 2010.
U.S. Appl. No. 12/682,327 (Forsell), filed Apr. 9, 2010.

* cited by examiner

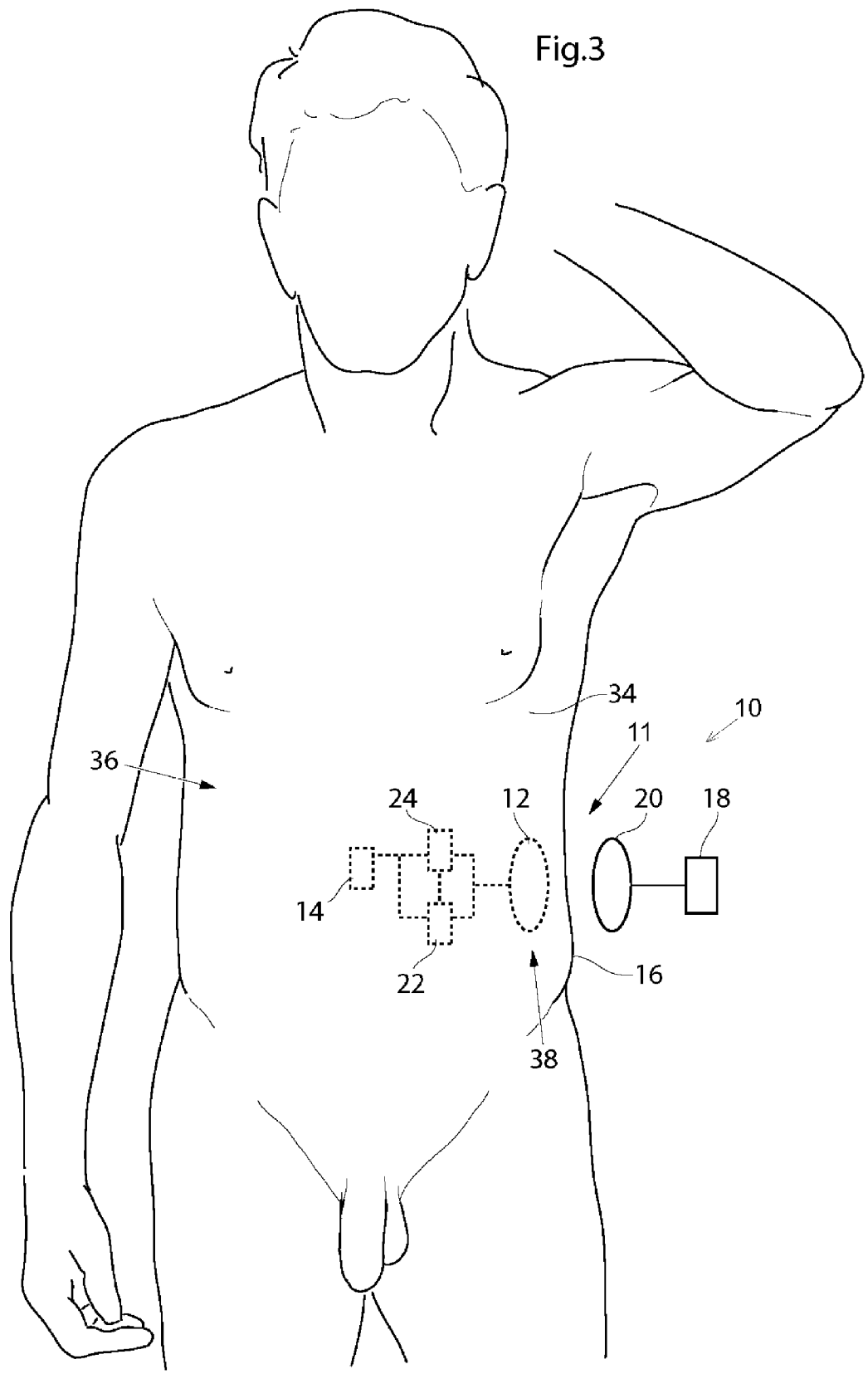

COIL SYSTEM

This application is the U.S. national phase of International Application No. PCT/SE2010/050857 filed 19 Jul. 2010 which designated the U.S. and claims the benefit of U.S. Provisional No. 61/213,804, filed 17 Jul. 2009; and which claims priority to Swedish Application No. 0901004-2 filed 17 Jul. 2009, the entire contents of each of which are hereby incorporated by reference.

TECHNICAL FIELD

The present invention relates to medical implants, and, more particularly, to coil systems for supplying energy or control signals to, or information from, a medical device implanted in a human or animal patient's body.

BACKGROUND

Medical devices are implanted in humans or animals for many reasons. Some of these devices are used to monitor one or more bodily functions. Other devices are used to stimulate or out rightly control bodily functions. Often, the medical devices will include some kind of communications circuit for receiving signals used to power and/or control the devices, or for sending outside a patient's body information about the medical device or bodily functions monitored or controlled by the device. Typically, medical devices are powered by an electric power supply, such as a battery, that provides the voltage and current needed for their operation.

Medical devices are often intended to be implanted in a patient's body for many years, and in some instances, for the rest of a patient's life. As such, the power supplies used to power these long-term medical devices are implanted in a patient at a location that permit easy access from outside the patient's body for recharging or replacement of the power supply. Typically, these power supplies are recharged by energy drawn from an alternating magnetic field generated outside of a patient's body and extending into inside of the patient's body using a pair of coils. The pair of coils includes a first or primary coil that generates the alternating magnetic field when an electric current is flowing therein and a second or secondary coil that is implanted in a patient's body. Alternatively, the second coil implanted in a patient's body may be connected directly to a power supply or to a medical device implanted in the patient. There can exist a problem that it is difficult to transfer sufficient amounts of energy for driving such a medical device. Thus, it would be desirable to provide a coil system including primary and secondary coils allowing a relatively high rate of energy transfer.

SUMMARY

The present invention is directed to coil arrangements or coil systems for supplying energy or control signals to, or providing information from, a medical device implanted in a human or animal patient where the medical device is used to monitor one or more bodily functions or to stimulate or out rightly control one or more bodily functions.

Thus generally, apparatus for supplying energy to a medical device implanted in a mammal patient comprises a coil arrangement including:

a first coil system external to the patient's body for wirelessly transmitting energy, and a second coil system that when implanted in the patient's body, receives wirelessly transferred energy for supplying energy or control signals to the medical device, when implanted in the patient's body, At least one of the first and second coil systems comprises a plurality of, i.e. at least two, individual coils. These coils are not directly electrically connected to each other. They operate basically independently of each other. Thus, each of the plurality of individual coils can be connected to a respective electric circuit and then each of these respective electric circuits operate basically independently of each other.

Each of the respective electric circuits can then generate an alternating electric current so that the currents generated for and supplied to different coils having different frequencies.

Each of the respective electric circuits can then be arranged for receiving on different frequencies.

In an alternative embodiment the apparatus for supplying energy to a medical device implanted in a mammal patient, the apparatus comprising:

a first coil system external to the patient's body for wirelessly transmitting energy for powering the medical device, a second coil system that when implanted in the patient's body, receives wirelessly transferred energy for supplying energy or control signals to the medical device, when implanted in the patient's body, wherein at least one of the first and second coil systems comprise a plurality of individual coils which in terms of frequency tuned energy supply operate basically independently of each other, for improving energy transmitting capacity, when implanted.

In an alternative and preferred embodiment the coil systems are working independently, but both at least two coil systems are connected to the same electronic circuit. The coil systems are preferable tuned with a capacitor so to have the sending outer coil tuned with the same frequency as the receiving coil, but the different integrated coil systems tuned with different frequencies. Thus, reducing the amount of energy field the patient have to tolerate at each frequency span, thus allowing higher energy transmission. The electric circuit may comprise a separate rectifier system for each coil system. They may be integrated in one common energy supply to an implant. Two or more different batteries connected in series may be used.

The apparatus may have each of said plurality of individual coils connected to one common electric circuit, handling the different tuned frequency supplies of energy. The apparatus may have each of said plurality of individual coils connected the electric circuit generating an alternating electric current, the currents generated for different coils having different frequencies. The apparatus may have each of said plurality of individual coils connected to the electric circuit for receiving on different frequencies.

The apparatus preferable have each of said plurality of individual coils connected to different rectifiers of the electric circuit for receiving on different frequencies. The different rectifiers may supply energy to two or more different batteries supplying energy to an implant and connected in series after each other. The different rectifiers are preferable integrated in one electronic circuit solution for one energy supply. A switched coil may be used in such integration. Each of said plurality of individual coils are preferable tuned with a capacitor connected in parallel over the coil, wherein each coil system comprising said sending outer coil and receiving inner coil are tuned at a different frequency.

In the case where the second coil system is implanted in a patient to supply energy to an energy-consuming implanted medical device, the second coil system can be connected to an implanted control device which, in turn, is connected to an implanted power supply connected to an implanted medical device, or directly to the implanted medical device. Alternatively, the second coil system can be connected to the implanted power supply connected to the medical device, or directly to the implanted medical device.

In the case where the second coil system is implanted in a patient to receive control signals for controlling the operation of an implanted medical device, the implanted second coil system is preferably connected to an implanted control device that is a receiver which, in turn, is connected to the implanted medical device. In the case where the implanted coil also transmit information from the implanted medical device, the second coil system can be connected to an implanted control device that is a transceiver which, in turn, is connected to the implanted medical device. The transceiver functions to receive control signals received by the second coil system and to provide informational signals to the second coil for transfer outside the patient's body.

BRIEF DESCRIPTION OF THE DRAWINGS

FIG. 3 is a schematic diagram showing the coil arrangement of any of FIGS. 2A-2F and the apparatus of FIG. 1 implanted in the body of a human patient.

DETAILED DESCRIPTION

Figure 1:
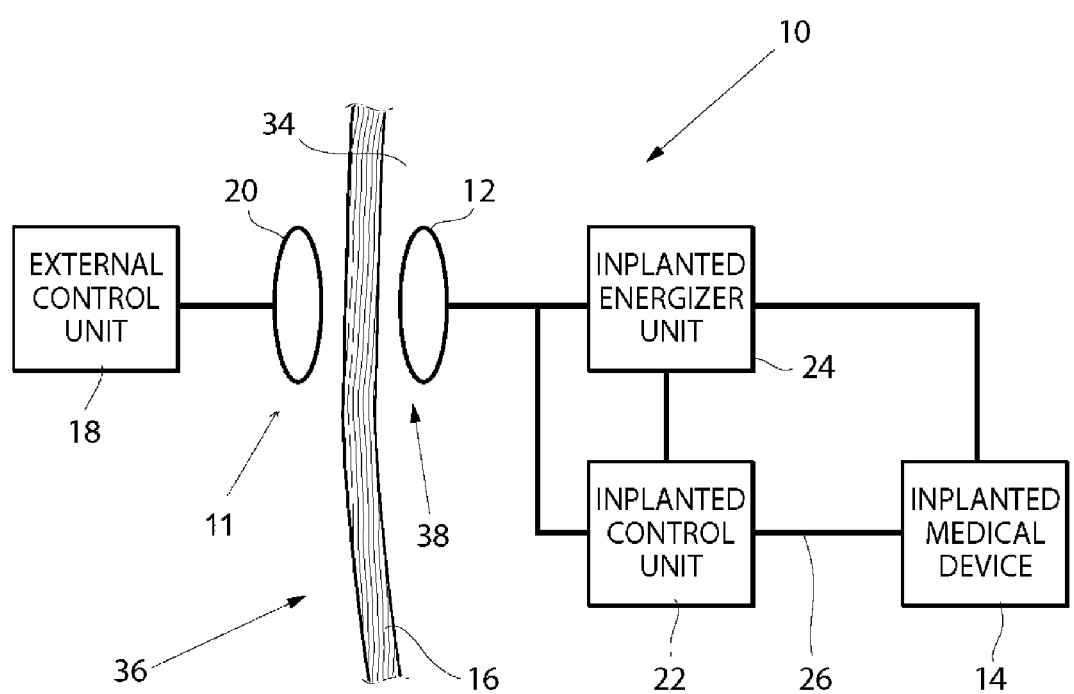
FIG. 1 is a schematic of apparatus for supplying energy or control signals to, or information from, a medical device implanted in a human or animal patient's body.

FIG. 1 is a schematic diagram of an apparatus 10 using a coil arrangement 11 to supply energy and/or control signals to and/or information from a medical device 14 implanted in a human or animal patient's body. FIG. 1 shows the basic park of the apparatus 10. All park placed to the left of the patient's skin 16 are located outside the patient's body and all park placed to the right of the skin 16 are implanted in the patient's body.

The coil arrangement 11 includes a first or primary coil system 20 and a second or secondary coil system 12, the first and second coils systems functioning as electrical conductors inductively coupled to each other, forming a transformer like circuit or transformer like circuit for the purpose of transferring alternating electrical energy signals into and out of a patient's body that supply energy or control signals to, or information from, the medical device 14 implanted in the patient's body 36.

The coil arrangement 11 has many similarities with an electrical transformer. An electrical transformer is an electrical device that transfers electrical energy from one circuit to another circuit through inductively coupled electrical conductors that may be formed into coils. An alternating current in a first winding or circuit of the transformer, often called the primary circuit, creates an alternating magnetic field, which induces an alternating voltage in a second winding or circuit of the transformer, often called the secondary circuit. An electric current, derived from induced alternating voltage, can then flow in the secondary winding or circuit to a load circuit connected to the secondary circuit, so as to transfer energy from the primary circuit through the secondary circuit to the load circuit connected to secondary circuit.

The apparatus 10 includes an external control unit 18 located outside of the patient's body. The external control unit 18 typically comprises a generator for generating an alternating electromagnetic signal, a modulator circuit and a power amplifier. The external control unit 18 may include a microprocessor for generating control signals to be sent to the implanted medical device 14. The microprocessor is capable of switching the generator on and off and of controlling the modulator circuit to modulate signals generated by the generator to send control information to the implanted medical device 14 via the power amplifier and a transmitting coil system 20 connected to the power amplifier in the external control unit 18. In the case where the external control unit 18 is a transceiver that functions to both transmit control signals to the implanted medical device 14 and receive information signals from the implanted medical device 14, the external control unit 18 also includes a demodulator that is connected to the first coil system 20, which receives the information sent from the implanted medical device 14. The demodulator demodulates information signals received by the first coil system 20 so as to strip out the information sent from the implanted medical device 14. Typically, such information will relate to bodily functions being monitored by the implanted medical device or the results of bodily functions controlled by the implanted medical device.

Implanted in the patient's body is an implanted control unit 22, which is connected to the implanted coil system 12. In the case where the second, implanted coil 12 is used to supply energy to the implanted medical device 14, the implanted control unit 22 may e.g. include a rectifier circuit for converting alternating signals received by the second coil system 12 into a direct current signal that is suitable for either powering the operation of the implanted medical device 14 or for charging an implanted rechargeable energizer unit 24 that powers the operation of the implanted medical device 14.

In the case where the second coil system 12 is used to receive control signals from the external control unit 18 and to transmit information signals from the implanted medical device 14 to the external control unit 18, the implanted control unit 24 will further comprise a demodulator and a microprocessor. The demodulator demodulates signals sent from the external control unit 18. The microprocessor receives the demodulated signal and sends control signals via a control line 26 to the implanted medical device to control its operation.

In the case where the implanted control unit 22 is a transceiver that functions to both receive control signals from the external control unit 18 and transmit information from the implanted medical device 14, the implanted control unit 22 will also include a generator for generating an alternating electromagnetic signal, a modulator circuit for modulating the generated alternating electromagnetic signal and a power amplifier connected to the implanted coil 12. The microprocessor is capable of switching the generator on and off and of controlling the modulation circuit to modulate the signals generated by the generator to send information from the implanted medical device 14 via the power amplifier and the second, implanted coil system 12 connected to the power amplifier to the external control unit 18.

Figure 2A:
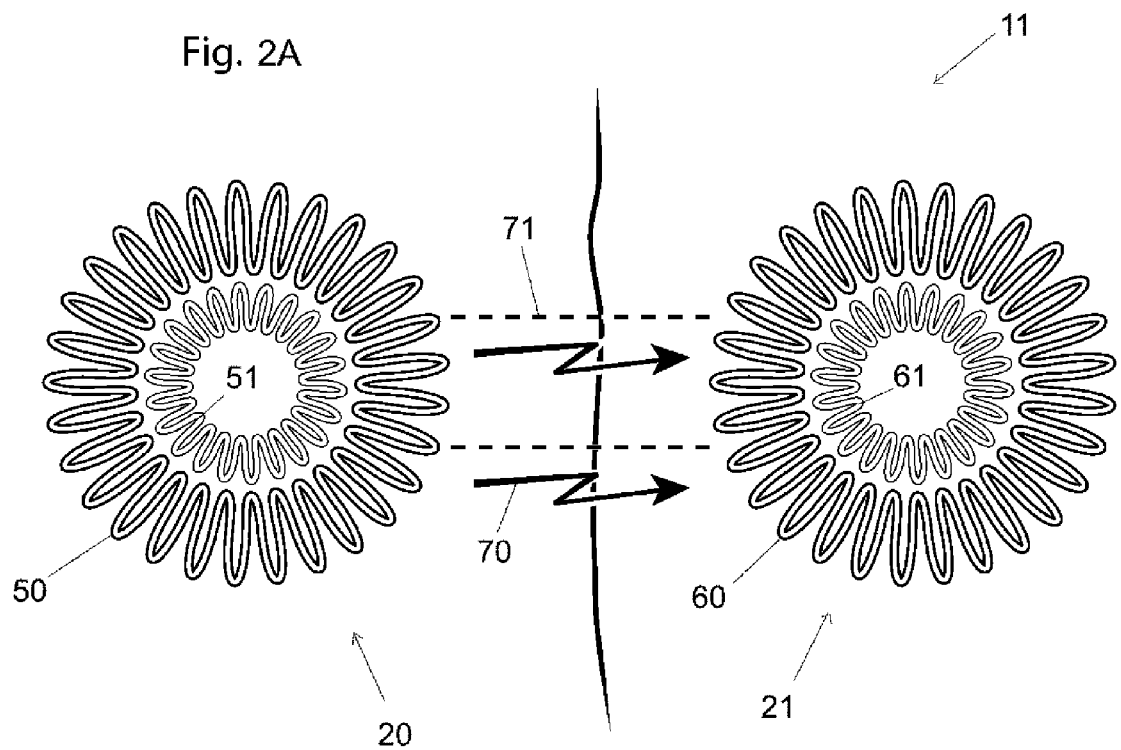
FIG. 2A is a schematic of the configuration and location of coils included in a coil arrangement used in the apparatus of FIG. 1 illustrating transfer of energy and information.

FIG. 2A is a schematic of a coil arrangement 11 comprising a first coil system 20 comprising generally two or more individual coils 50, 51 and a second, implanted coil system 2 generally comprising two or more individual, implanted coils 60, 61. The wireless energy transfer from the first coil system 20 to the second coil system 12 is indicated by the arrows 70 and the transfer of signals between the two coil systems is indicated by the dashed lines 71.

Each of the individual coils 50, 51 of the first coil system 20 can be connected to an own generator for generating an alternating electromagnetic signal and also, an own modulator circuit when required and an own power amplifier when required. The individual generators can then generate alternating electromagnetic signals of frequencies that are different from each other so that one coil 50 is supplied with an alternating electromagnetic signal of a first frequency and another coil 51 is supplied with an alternating electromagnetic signal of a second frequency different from the first frequency.

The microprocessor in the external control unit 18 can then be capable of switching each of the generators on and off and of controlling the respective modulator circuit to modulate signals generated by the generators to send control information to the implanted medical device 14 via respective power amplifiers if required and the coils of the transmitting, first coil system 20.

In the case where the external control unit 18 is a transceiver that functions to both transmit control signals and receive information signals, the external control unit 18 also includes individual, respective demodulators connected to the individual coils of the first coil system 20, which receive the information sent from the implanted medical device 14. The demodulators demodulate information signals received by coils of the first coil system 20 to extract the information sent from the implanted medical device 14.

In the case where the second, implanted coil system 12 is used to supply energy to the implanted medical device 14, each of the individual coils 60, 61 of the second coil system 12 can be connected to respective, individual rectifier circuits for converting alternating signals received by the respective coil of the second coil system 12 into a direct current signal that is suitable for either powering the operation of the implanted medical device 14 or for charging an implanted rechargeable energizer unit 24 that powers the operation of the implanted medical device 14.

In the case where the second coil system 12 is used to receive control signals from the external control unit 18, the implanted control unit 24 comprises individual demodulators connected to the coils 60, 61 of the second coil system, one demodulator arranged for and connected to each of the coils. The demodulators demodulate signals sent from the external control unit 18 and forwards them to the microprocessor included in the implanted control unit.

In the case where the implanted control unit 22 is a transceiver that functions to both receive control signals from the external control unit 18 and transmit information from the implanted medical device 14, the implanted control unit 22 also includes for each of the coils 60, 61 in the second coil system 12 an individual generator for generating alternating electromagnetic signals, the signals generated by one of such generators having wavelengths that are different from those generated by the other of such generators. For each of the coils also an individual modulator circuit for modulating the generated alternating electromagnetic signal is arranged and a power amplifier connected to the respective implanted coil 60, 61 can be provided when required. The microprocessor in implanted control unit 22 is capable of switching the generators on and off and of controlling the individual modulation circuits to modulate the signals generated by the respective generator to send information from the implanted medical device 14 via the power amplifier and the second, implanted coil system 12 to the external control unit 18.

Obvious alternatives to the above described total system for transferring energy and information include that only one of the individual coils 50, 51 of the first coil system 20 and only one of the individual coils 60, 61 of the second coil system are used to transfer information, or that only one of the individual coils 50, 51 of the first coil system 20 is used to transfer information to one of the individual coils 60, 61 of the second coil system 12 and another of the individual coils 60, 61 of the second coil system is used to transfer information in the opposite direction to another of the individual coils 50, 51 of the first coil system 20.

Then, obviously, modulators and demodulators are only provided where required.

Thus, the individual coils of the first coil system 20 and the individual coils of the second coil system can be arranged in pairs, so that each pair comprises one coil in the first coil system and one coil in the second system, each coil only included in one pair. The transfer of energy and/or information between the coils in one pair is made using frequencies that are different from the frequencies used by the other pair or the other pairs.

Figure 2B:
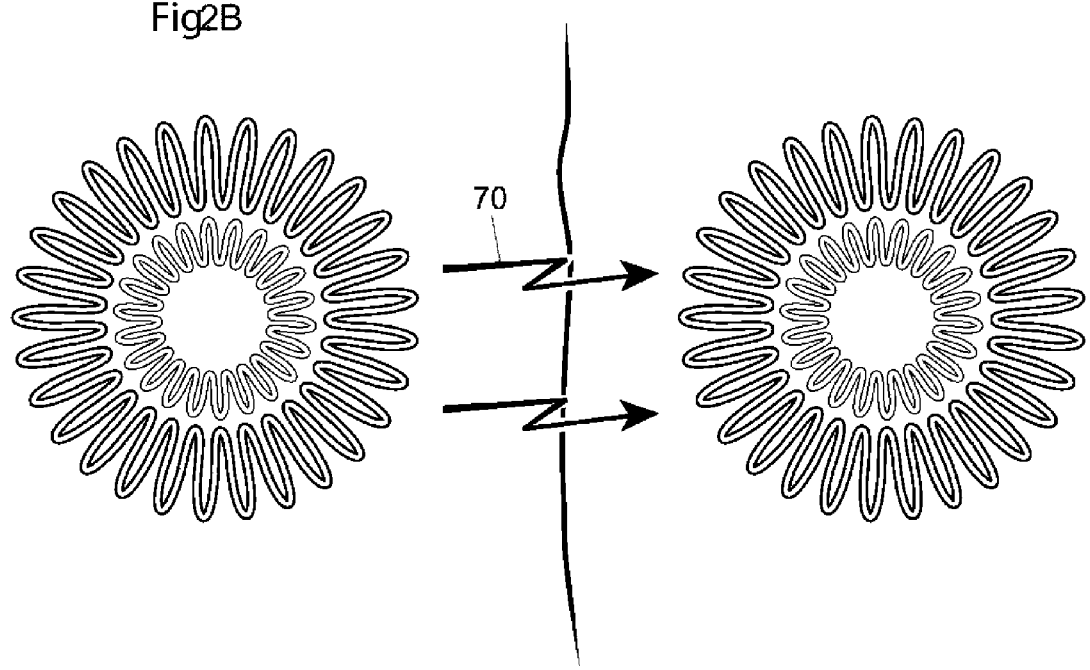
FIG. 2B is similar to FIG. 2A but illustrating only transfer of energy.

The individual coils of the first and second coil systems 20, 12 can have different geometric configurations as illustrated in the schematics of FIGS. 2A-2F. Each of the coils is as conventional formed from an electrically conducting wire. As seen in FIGS. 2A and 2B the coils 50, 51; 60, 61, also called windings, can have a generally toroidal shape. Such a coil is formed from a wire that is helically wound around a toroidal axis that has the shape of a closed curve. The toroidal axis can be substantially flat. It can e.g. as illustrated be a circle. The toroidal axes of the coils included in each of the first and second coils systems 20, 12 can be located in the same plane. As illustrated, the toroidal axes of the coils included in each of the first and second coils systems 20, 12 can also be concentric so that an inner coil 51; 61 has a toroidal axis of a size or diameter that is smaller than that of an outer coil 50; 51. The inner coil can then be located completely separated from the outer coil, such as inside the outer coil as illustrated.

Figure 2C:
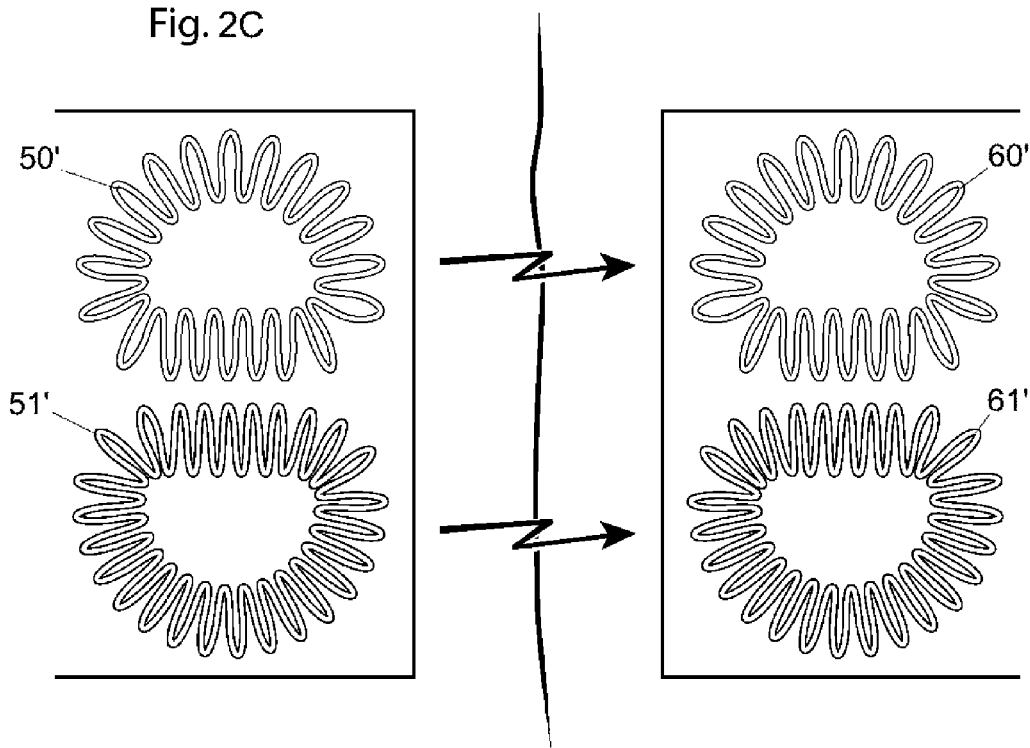
FIGS. 2C-2F are similar to FIG. 2B of coils having various alternative configurations and locations.
Figure 2D:
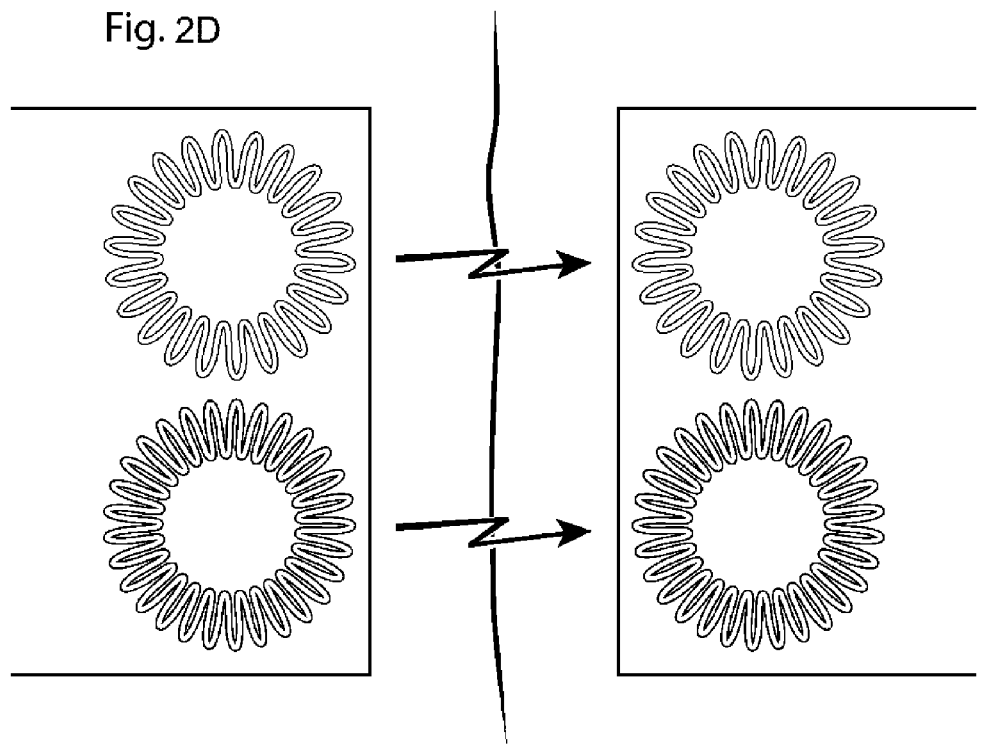
Figure 2E:
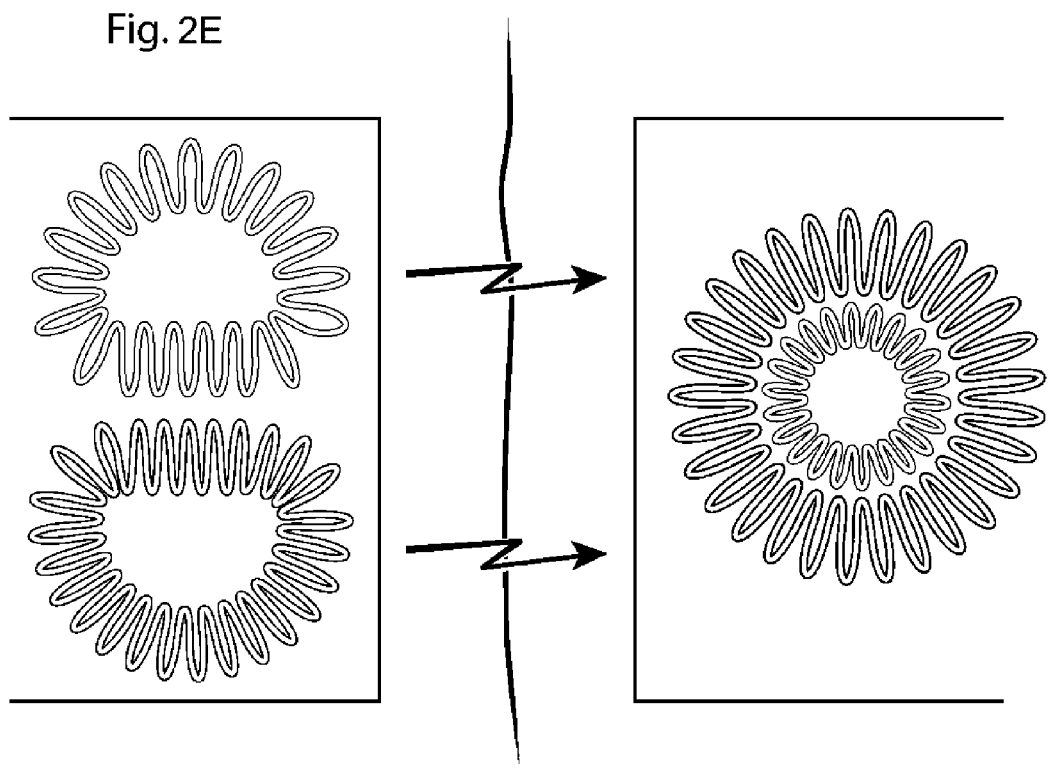

The individual coils seen in FIGS. 2C and 2D included in one of the first and second coil systems 20, 12 are also located completely separated from each other. They are also located in the same plane but in these cases at the sides of each other and can then both have the same basic shape and size. The coils 50', 51'; 60', 61' of FIG. 2C have toroidal axes that include a substantially straight segment whereas the rest of the respective axis is curved, such as having a substantially part-circular or part-elliptic shape. The straight segments of the two coils in one of the first and second coil systems can then be parallel to each other and located adjacent to or facing each other.

As seen in FIG. 2D the coils included in the first coil system 20 can have a configuration that is different from, even quite different from, the configuration of the coils included in the second coil system 12.

Figure 2F:
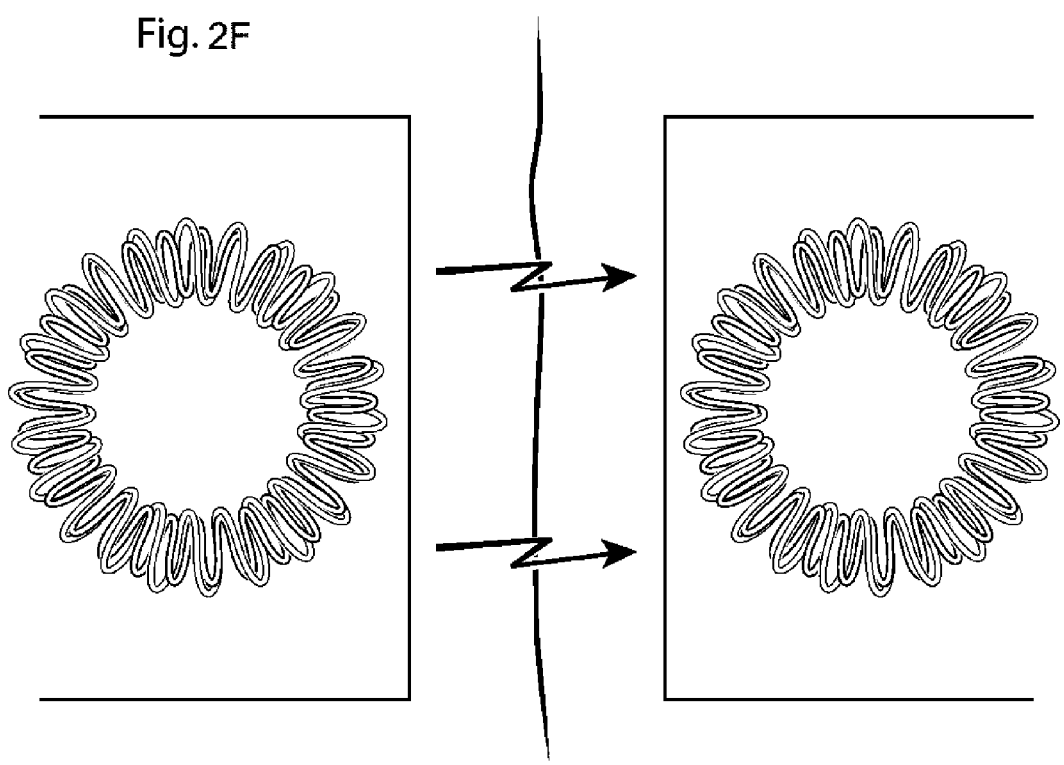

The coils included in one of the first and second coil systems 20, 12 can also, as seen in FIG. 2F, be located so that the electrically conducting wire of one of the coils is intermeshed with or entangled with the wire of another of the coils. Thus, the two coils can have the same toroidal axis but e.g. different diameters of the helical winding. Also, the pitch of the helical windings can be different.

FIG. 3 is a schematic diagram showing a coil arrangement 11 according to any of FIGS. 2A-2F and the apparatus 10 of FIG. 1 implanted in the body 34 of a human patient 36. As shown in FIG. 3, the second coil system 12 is implanted in the body 34 of patient 36 at a location 38 that may permit easy access to the second coil system from outside the patient's body 34. For example, the coil 12 can be implanted subcutaneously in the skin 16 of the patient 36 at a location for such easy access. Then, the implanted control unit 22 and the rechargeable energizer unit 24 can also be located at an easy access location within the body 34 of the patient 36 and then connected by one or more wires to the implanted medical device 14.

It should be noted that FIGS. 1, 2A-2F and 3 are not intended to depict a particular orientation of the external coil system 20 and/or the implanted coil system 12 with respect to the body of a patient with whom these devices are used. Rather, it should be noted that either or both of these devices can be oriented horizontally, vertically or otherwise with respect to the body of a patient to accommodate the needs of a particular application in which these devices are used. Furthermore, the coil system . . . itself could be done any one of many different ways. Preferably, the coil winding is compact with the windings concentrated in a small transversal area. A core could also be used with the coil, but it is not required. If such a coil were to be implanted in a patient with a substantially horizontal orientation vis-à-vis the substantially vertical orientation of the patient, when standing, the coil would preferably be very low in subcutaneous height, thereby avoiding protruding material under the skin.

While the invention has been described in connection with what is presently considered to be the most practical and preferred embodiment, it is to be understood that the invention is not to be limited to the disclosed embodiment, but on the contrary, is intended to cover various modifications and equivalent arrangement included within the spirit and scope of the appended claims.

The invention claimed is:

1. Apparatus for supplying energy to a medical device implanted in a mammal patient, the apparatus comprising:
   a first coil system external to the patient'Ls body for wirelessly transmitting energy for powering the medical device,
   a second coil system that, when implanted in the patients body, receives wirelessly transferred energy for supplying energy or control signals to the medical device, when implanted in the patients body,
   wherein at least one of the first and second coil systems comprise a plurality of individual coils which in terms of frequency tuned energy supply operate basically independently of each other, for improving energy transmitting capacity, when implanted,
   wherein two or more coils in the first coil system and two or more coils in the second coil system are adapted to cause a transfer of energy from outside the body to the inside thereof, for powering the medical device,
   wherein each of said plurality of individual coils are tuned with a capacitor connected in parallel over the coil,
   wherein at least one first coil in the first coil system and at least one second coil in the second coil system are tuned to a first frequency, and
   wherein at least one third coil in the first coil system and at least one fourth coil in the second coil system, are tuned to a second frequency being a different frequency than the first frequency.

2. The apparatus of claim 1, wherein each of said plurality of individual coils are connected to a respective electric circuit, each of these respective electric circuits operating basically independently of each other.

3. The apparatus of claim 1, wherein each of said plurality of individual coils are connected to a respective electric circuit generating an alternating electric current, the currents generated for different coils having different frequencies.

4. The apparatus of claim 1, wherein each of said plurality of individual coils are connected to electric circuits are connected to a respective electric circuit for receiving on different frequencies.

5. The apparatus of claim 1, wherein each of said plurality of individual coils are connected to one common electric circuit, handling the different tuned frequency supplies of energy.

6. The apparatus of claim 5, wherein each of said plurality of individual coils are connected the electric circuit generating an alternating electric current; the currents generated for different coils having different frequencies.

7. The apparatus of claim 1, wherein each of said plurality of individual coils are connected to one common electric circuit for receiving on different frequencies.

8. The apparatus of claim 5, wherein each of said plurality of individual coils are connected to different rectifiers of the electric circuit for receiving on different frequencies.

9. The apparatus of claim 8, wherein said different rectifiers and the electric circuit is adapted to supply energy to two different batteries for indirect energy supply, the batteries connected in series after each other.

10. The apparatus of claim 8, wherein the different rectifiers are integrated in one electronic circuit solution for one energy supply.

11. The apparatus of claim 1, wherein at least one of the following alternatives apply:
   the first coil in the first coil system is tuned to the same frequency as the second coil and at least one more coil in the second coil system,
   the second coil in the second coil system is tuned to the same frequency as the first coil and at least one more coil in the first coil system.

12. The apparatus of claim 1, wherein said plurality of individual coils include toroidal coils having toroidal axes having the shapes of closed curves, in particular circular toroidal axes, the toroidal axes being concentric with each other.

13. The apparatus of claim 12, wherein said plurality of individual coils include toroidal coils having toroidal axes having the shapes of closed curves, in particular circular toroidal axes, the toroidal axes having different sizes or diameters, the toroidal axis of one of the coils being located inside the toroidal axis of another of the coils.

14. The apparatus of claim 1, wherein said plurality of individual coils include toroidal coils, each having the same toroidal axis.

15. The apparatus of claim 1, wherein said plurality of individual cods include toroidal coils having toroidal axes having the shapes of closed curves, the closed curves being substantially flat and located in the same plane.

16. The apparatus of claim 1, further comprising a second control unit that, when implanted in the patients body, is connected to the second coil system so as to receive energy or control signals from the second coil system or to provide information signals to the second coil system for transmission to the first coil system.

17. The apparatus of claim 16, further comprising a first control unit that is located outside the patient's body and is connected to the first coil system and
   that generates energy or control signals for transfer to the second coil system or receives information signals transmitted from the second coil system.

18. The apparatus of claim 17, wherein the signal generated by the first control unit is an alternating current that flows through at least one of the coils included in the first coil system, and wherein the energy wirelessly received by one of the coils of the second coil system is carried by an alternating magnetic field, which is
- created by the alternating current flowing in said at least one of the coils included in the first coil system and which induces an alternating voltage in said one of the coils of the second coil system.

19. The apparatus of claim 18, wherein the alternating voltage induced in said one of the coils of the second coil system causes an electric current to flow to a load circuit connected to said one of the coils of the second coil system, so as to
- transfer energy from said at least one of the coils included in the first coil system through said one of the coils of the second coil system to the load circuit connected to said one of the coils of the second coil system.

20. The apparatus of claim 19, wherein the load circuit is a power supply that, when implanted in the patients body, supplies energy to the implanted medical device.

* * * * *